United States Patent [19]

Han et al.

[11] Patent Number: 4,973,784
[45] Date of Patent: Nov. 27, 1990

[54] PROCESS FOR REDUCING THE DURENE CONTENT OF EFFLUENT RESULTING FROM THE CATALYTIC CONVERSION OF $C_1$-$C_4$ OXYGENATES TO GASOLINE

[75] Inventors: Scott Han, Lawrenceville; Clarence D. Chang, Princeton, both of N.J.

[73] Assignee: Mobil Oil Corp., Fairfax, Va.

[21] Appl. No.: 449,169

[22] Filed: Dec. 13, 1989

Related U.S. Application Data

[63] Continuation-in-part of Ser. No. 254,524, Oct. 6, 1988, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .................................................. C07C 4/18
[52] U.S. Cl. ..................................... 585/475; 585/470; 585/471
[58] Field of Search ................ 585/469, 470, 471, 475

[56] References Cited

U.S. PATENT DOCUMENTS

| | | | |
|---|---|---|---|
| 3,894,102 | 7/1975 | Chang et al. | 260/668 R |
| 3,894,104 | 7/1975 | Chang et al. | 260/668 R |
| 3,899,544 | 8/1975 | Chang et al. | 260/668 R |
| 3,904,916 | 9/1975 | Emidy et al. | 313/493 |
| 3,911,041 | 10/1975 | Kaeding et al. | 260/682 |
| 3,931,349 | 1/1976 | Kuo | 260/668 R |
| 3,969,426 | 7/1976 | Owen et al. | 260/668 R |
| 4,025,576 | 5/1977 | Chang | 260/682 |
| 4,347,397 | 8/1982 | Dwyer et al. | 585/469 |
| 4,387,261 | 6/1983 | Chester et al. | 585/469 |
| 4,439,409 | 3/1984 | Puppe et al. | 423/328 |
| 4,577,049 | 3/1986 | Rudnick | 585/475 |
| 4,717,780 | 1/1988 | Olson et al. | 585/467 |
| 4,826,667 | 5/1989 | Zones et al. | 423/277 |
| 4,891,458 | 1/1990 | Innes et al. | 585/475 |

FOREIGN PATENT DOCUMENTS

| | | | |
|---|---|---|---|
| 231860 | 8/1987 | European Pat. Off. | 502/64 |
| 293032 | 11/1988 | European Pat. Off. | 502/64 |

*Primary Examiner*—Anthony McFarlane
*Attorney, Agent, or Firm*—Alexander J. McKillop; Charles J. Speciale; Dennis P. Santini

[57] ABSTRACT

A reduction in the durene content of an effluent resulting from the zeolite-catalyzed conversion of a $C_1$-$C_4$ oxygenate such as methanol to gasoline is disclosed wherein either the total effluent from said conversion or a bottoms fraction thereof containing durene is contacted with a particular zeolite catalyst to convert said durene to other products.

21 Claims, No Drawings

PROCESS FOR REDUCING THE DURENE CONTENT OF EFFLUENT RESULTING FROM THE CATALYTIC CONVERSION OF $C_1-C_4$ OXYGENATES TO GASOLINE

CROSS-REFERENCE TO RELATED APPLICATIONS

This application is a continuation-in-part of U.S. patent application Ser. No. 254,524, filed Oct. 6, 1988, pending, as a continuation-in-part of U.S. patent application Ser. No. 98,176, filed Sept. 18, 1987, now abandoned, which is a continuation-in-part of U.S. patent application Ser. No. 890,268, filed July 29, 1986, now abandoned.

BACKGROUND OF THE INVENTION

This invention relates generally to the zeolite catalyzed conversion of one or more $C_1-C_4$ oxygenates such as methanol to hydrocarbons boiling within the gasoline range and, more particularly, to the treatment of all or a portion of a durene-containing effluent or fraction resulting from said conversion in order to reduce its durene content.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

The conversion of $C_1-C_4$ oxygenates such as methanol to gasoline is an important area of technology which has the potential of becoming even more important as the supply of crude oil is diminished and/or increased in price. Particularly advantageous catalysts which are utilized in the conversion of $C_1-C_4$ oxygenates to gasoline are a special class of porous, acidic crystalline silicate, or zeolite, catalysts of which HZSM-5 is the most preferred member. There are many patents and publications which describe the conversion of oxygenates to gasoline over the zeolites, among them U.S. Pat. Nos. 3,894,102; 3,894,104; 3,899,544; 3,904,916; 3,911,041; 3,931,349; and, 3,969,426, the disclosures of which are incorporated by reference herein.

One particular problem residing in the conversion of $C_1-C_4$ oxygenates to gasoline over such zeolites, e.g. ZSM-5, is that durene is produced in amounts higher than that expected from $C_{10}$ aromatic equilibrium distributions. Once an aromatic ring is formed in the presence of unreacted methanol, alkylation to tetramethylbenzenes occurs rapidly but the smaller, higher melting durene molecule (1,2,4,5-tetramethylbenzene, melting point 175° F.) diffuses out of the ZSM-5 pores much more rapidly than isodurene (1,2,3,5-tetramethylbenzene). Durene is an undesirable high boiling aromatic with a tendency to crystallize out at low temperatures thus forming a solid film on heat exchanger tubes and process lines, often breaking up into a sludge which plugs the lines through which it is passed.

Various proposals have been advanced for dealing with durene which is produced in the catalytic conversion of $C_1-C_4$ oxygenates to gasoline, the proposals generally falling into two broad categories. One approach to the problem is to vary the conversion conditions so that durene is either not formed at all or, at most, is formed only in small amounts. An approach of this type is represented by U.S. Pat. No. 4,025,576 which discloses that durene formation is reduced if methanol is first converted to olefins in a first stage and the olefins are thereafter converted to gasoline range hydrocarbons in a second stage.

The second approach with regard to durene control makes no attempt to control the amount of durene which is formed in the conversion of $C_1-C_4$ oxygenates to gasoline but seeks to convert at least some of the durene to other products. This is the approach taken in the processes disclosed in aforementioned U.S. Pat. Nos. 3,969,426 and 4,347,397.

As disclosed in U.S. Pat. No. 3,969,426, the durene produced in a methanol to gasoline conversion process is diminished by reacting a durene-containing stream with one or more low boiling aromatics, e.g., benzene, in order to transalkylate, and thereby reduce, the durene content of the stream. A disadvantage of this process lies in the fact that in the ZSM-5 catalyzed conversion of methanol to gasoline such as described in this patent, little benzene is produced. Therefore, in order to carry out the durene-reduction process of U.S. Pat. No. 3,969,426, an external source of benzene must be made available for reaction with the durene-containing component of the methanol to gasoline conversion process effluent. This drawback is obviated by the process of U.S. Pat. No. 4,347,397 which does not require benzene (or other transalkylating aromatic) and, in fact, is preferably conducted in the substantial absence of benzene, i.e., with no more than about 5 wt.%, and preferably no more than about 1 wt.% benzene, being present.

In accordance with the process disclosed in aforesaid U.S. Pat. No. 4,347,397, the total durene-containing effluent from a methanol to gasoline conversion process or a durene-containing bottoms fraction thereof (obtained from the total gasoline fraction by topping off at least a light olefinic fraction) is treated by isomerization at elevated temperature and pressure over known and conventional isomerization catalysts including amorphous catalysts such as silica-alumina, silica-magnesia, silica-zirconia, silica-alumina-magnesia, silica-alumina-zirconia, metal phosphates, etc., as well as crystalline aluminosilicate zeolites such as zeolite X, Y, ZSM-4, Zeolite Beta, ZSM-11, ZSM-12, etc., to isomerize durene to other tetramethylbenzene, 1,2,3,5-tetramethylbenzene but some 1,2,3,4-tetramethylbenzene as well, both of which have lower melting points than durene.

SUMMARY OF THE INVENTION

In accordance with the present invention, a process for reducing the durene content of a durene-containing effluent or durene-containing fraction thereof resulting from the zeolite-catalyzed conversion of at least one $C_1$-$C_4$ oxygenate to gasoline is provided which comprises contacting said durene-containing effluent or durene-containing fraction under durene conversion conditions with a durene conversion catalyst to convert the durene to one or more other products, said catalyst comprising a synthetic porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

Unlike the durene conversion process of U.S. Pat. No. 4,347,397 in which durene is transalkylated to other tetramethylbenzene isomers, notably, 1,2,5- and 1,2,3,4-tetramethylbenzenes, the durene process of this invention does not appear to involve transalkylation of durene to any appreciable extent but instead, appears to result in the disproportionation of durene to other methylbenzenes such as toluene, xylenes and trimethylbenzenes. Regardless of the actual nature of the reaction mechanism or mechanisms involved, it remains that the nature and amount of durene conversion products obtained by the process of the present invention are distinctly different from those resulting from the practice of the durene conversion process of U.S. Pat. No. 4,347,397.

DESCRIPTION OF SPECIFIC EMBODIMENTS

The entire contents of applications Serial Nos. 254,524; 98,176; and 890,268 are incorporated herein by reference.

The process of this invention is applicable to both fixed bed and fluid bed processes and a convenient way of carrying out the process is to cascade the total effluent from a process for converting $C_1$-$C_4$ oxygenate(s) to gasoline through a separate reactor or a separate zone containing the durene conversion catalyst hereinafter more fully described in order to effect conversion of the durene to other products.

The process of this invention is carried out at temperatures ranging from about 200° to about 1000° F. and more preferably from about 600° to about 900° F., pressures ranging from about 0 to about 1000 psig and more preferably from about 15 to about 300 psig, a mole ratio of hydrogen to hydrocarbons of from about 0 (i.e., no added hydrogen is present) to about 10 and preferably from about 1 to about 3, and at weight hourly space velocities (WHSV) ranging from about 0.1 to about 100 hr$^{-1}$ and more preferably from about 0.1 to about 10 hr$^{-1}$.

Particularly preferred embodiments of this invention reside in subjecting the total gasoline derived from the conversion of $C_1$-$C_4$ oxygenate(s) to a distillation process or a fractionation process in order to remove at least the light olefinic fractions. It may not always be advantageous to treat the total gasoline fraction since, quite obviously, the durene is concentrated at the higher boiling end and not at the light end. The exact point at which the total gasoline can be cut to provide a heavy fraction in which the durene is concentrated is not narrowly critical and a dividing point can be at a temperature ranging from about 200° to about 400° F. A more preferred cut point is from about 300° to about 400° F. with a still more preferred cut point being at about 350° F. to about 400° F.

The principal conversion products of durene resulting from the process of this invention include toluene, xylenes and trimethylbenzenes. The percentage conversion of durene to such products will vary depending on the specific circumstances of a particular durene conversion operation with conversion levels of at least about 30 wt.%, preferably at least about 50 wt.% and more preferably still, at least about 70 wt.%, being readily achievable.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | V-S |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |

TABLE D-continued

| Interplanar d-Spacing (A) | Relative Intensity, $I/I_o \times 100$ |
|---|---|
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the stongest line or peak, and d (obs.) the interplanar spacing in Angstrom Units (A), corresponding to the recorded lines, were determined. In Tables A–D, the relative intensities are given in terms of the symbols W=weak, M=medium, S=strong, VS=very strong. In terms of intensities, these may be generally designated as follows:

| W | 0–20 |
| M | 20–40 |
| S | 40–60 |
| VS | 60–100 |

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for the present process. These include hydrogen rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use as durene conversion catalyst, the zeolite crystals should be subjected to thermal treatment to remove part or all of any organic constituent present therein.

The zeolite durene conversion catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation is desired. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing a platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the durene conversion process of this invention, the zeolite crystals should be at least partially dehydrated. This can be achieved by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
| --- | --- | --- |
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt.% solid $YO_2$. Where $YO_2$ is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the zeolite crystalline material into another material which is resistant to the temperatures and other conditions employed in the durene conversion process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that durene conversion products can be obtained economically and orderly without employing other means for controlling the rate of reaction. These materials may be incorporated into naturally occurring clays, e.g., bentonite and kaolin, to improve the crush strength of the catalyst under commercial durene conversion operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anaumite Such clays can be used in the raw state as originally mined or initially subjected to calcination, acid treatment or chemical modification. Binders useful for compositing with the zeolite also include inorganic oxides, notably alumina.

In addition to the foregoing materials, the zeolite crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix may vary widely, with the crystal content ranging from about 1 to about 90 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5–100% steam at a temperature of at least 300° C. (e.g. 300–650° C.) for at least one hour (e.g. 1–200 hours) at a pressure of 100–2,500 kPa. In a more particular embodiment, the catalyst can be made to undergo steaming with 75–100% steam at 315–500° C. and atmospheric pressure for 2–25 hours.

In order to more fully illustrate the durene conversion process of this invention and the manner of practicing same, the following examples are presented. In examples illustrative of the synthesis of zeolite, whenever sorption data are set forth for comparison of sorptive capacities for water, cyclohexane and/or n-hexane, they are Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor and 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt.% for water vapor, greater than about 4.5 wt.%, usually greater than about 7 wt.% for cyclohexane vapor and greater than about 10 wt.% for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis,* Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis,* Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | |
|---|---|
| $SiO_2/Al_2O_3 =$ | 30.0 |
| $OH^-/SiO_2 =$ | 0.18 |
| $H_2O/SiO_2 =$ | 44.9 |
| $Na/SiO_2 =$ | 0.18 |
| $R/SiO_2 =$ | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the calcined crystalline material was measured to be 494 $m^2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE E

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.1 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were analyzed by X-ray diffraction, sorption, surface area and chemical analyses and the results are presented in Table F. The sorption and surface area measurements were of the calcined product.

TABLE F

| | Example | | |
|---|---|---|---|
| | 3 | 4 | 5 |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results are set forth in Table G:

TABLE G

| Product Composition uncalcined | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material were ion-exchanged with 100 ml of 0.1N IEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649 °C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3$ = | 6.1 |
| $OH^-/SiO_2$ = | 0.06 |
| $H_2O/SiO_2$ = | 19.0 |
| $K/SiO_2$ = | 0.06 |
| $R/SiO_2$ = | 0.30 | where R is hexamethyleneimine.

the mixture was crystallized in a stainless steel reactor, with agitation, at 150° C. for 8 days. The crystalline product was filtered, washed with water and dried at 120 °C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405m$^2$/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = 1406 | |
| $SiO_2/(Al + B)_2O_3$, molar ratio = 25.8 | |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPlE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3$ = | 12.3 |
| $OH^-/SiO_2$ = | 0.056 |
| $H_2O/SiO_2$ = | 18.6 |
| $K/SiO_2$ = | 0.056 |
| $R/SiO_2$ = | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438$^2$/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = 249 | |
| $SiO_2/(Al + B)_2O_3$, molar ratio = 28.2 | |

EXAMPLE 14

A portion of the calcined crystalline product of Example 13 was tested in the Alpha Test and found to have an Alpha Value of 5.

EXAMPLES 15-29

These examples illustrate the present invention for the conversion of durene. The zeolite catalyst was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized H₂O and dried. A portion of the zeolite crystals was combined with Al₂O₃ to form a mixture of 65 parts, by weight, zeolite and 35 parts Al₂O₃. Water was added to this mixture to allow the resulting catalyst to be formed into extrudates. The catalyst was activated by calcining at 480° C. (900° F.) in 3v/v/min nitrogen for three hours, then treated with 50 vol.% air/50 vol.% N₂ at 3v/v/min, also at 480° C. (900° F.). The calcination was completed by raising the temperature to 540° C. (1000° F.) at 5° F./min and finally switching to 100% air (3v/v/min) and holding at 540° C. (1000° F.) for three hours.

The feed employed was a mixture of approximately 25 wt.% durene and 75 wt.% benzene. The temperature, pressure, hydrogen to hydrocarbon mole ratio and WHSV (based on zeolite) conditions and the product distributions obtained in each example are set forth in Table H as follows:

TABLE H

| EXAMPLE | Feed | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| CONDITIONS | | | | | | | | | | | | | | | | |
| Temperature, °F. | — | 601 | 700 | 700 | 700 | 801 | 802 | 802 | 802 | 802 | 802 | 802 | 802 | 849 | 849 | 849 |
| WHSV (zeolite) | — | 4.3 | 4.0 | 4.0 | 4.1 | 4.1 | 4.0 | 4.1 | 4.1 | 4.1 | 4.1 | 4.1 | 4.1 | 4.0 | 4.0 | 4.0 |
| Pressure, psig | — | 600 | 600 | 600 | 600 | 630 | 630 | 630 | 640 | 620 | 620 | 630 | 630 | 620 | 620 | 620 |
| H₂/HC mole ratio | — | 2 | 2 | 2 | 2 | 2 | 2 | 2 | 2 | 2 | 2 | 2 | 2 | 2 | 2 | 2 |
| PRODUCT DISTRIBUTIONS. wt. % | | | | | | | | | | | | | | | | |
| C₅— | — | 0.2 | 0.2 | 0.2 | 0.1 | 1.2 | 0.9 | 0.9 | 0.7 | 1.1 | 0.8 | 0.9 | 0.7 | 1.6 | 1.5 | 1.3 |
| Benzene | 7.2 | 70.6 | 69.2 | 70.6 | 71.6 | 66.1 | 63.9 | 63.7 | 66.0 | 66.3 | 63.9 | 64.0 | 69.0 | 62.8 | 63.5 | 61.4 |
| Toluene | — | 5.3 | 5.9 | 4.4 | 3.6 | 10.6 | 9.9 | 9.3 | 8.7 | 8.3 | 8.7 | 8.7 | 7.6 | 13.1 | 12.4 | 12.5 |
| Ethylebenzene | — | 0.1 | 0.2 | 0.2 | 0.2 | 0.9 | 0.8 | 0.7 | 0.6 | 0.6 | 0.6 | 0.6 | 0.5 | 1.0 | 1.0 | 1.0 |
| Xylenes | — | 1.5 | 1.6 | 1.1 | 0.9 | 2.0 | 3.7 | 3.5 | 3.3 | 3.1 | 3.3 | 3.3 | 2.7 | 4.8 | 4.5 | 4.6 |
| Ethyltoluenes | — | — | 0.1 | 0.1 | 0.2 | 0.1 | 0.1 | 0.1 | 0.1 | 0.1 | 0.1 | 0.1 | 0.1 | 0.1 | 0.1 | 0.1 |
| Trimethylbenzenes | 0.2 | 5.9 | 7.2 | 5.7 | 4.7 | 8.5 | 8.8 | 8.7 | 8.1 | 7.8 | 8.6 | 8.6 | 7.2 | 8.1 | 7.9 | 8.5 |
| Durene | 24.6 | 14.5 | 13.7 | 15.5 | 16.5 | 9.0 | 10.3 | 1.3 | 10.8 | 10.9 | 12.0 | 11.9 | 10.6 | 7.3 | 7.8 | 9.1 |
| Unknown Fractions | — | 1.9 | 1.9 | 2.2 | 2.3 | 1.5 | 1.6 | 1.8 | 1.7 | 1.8 | 2.0 | 1.9 | 1.6 | 1.2 | 1.3 | 1.5 |
| % Durene Converted | | 41.1 | 44.3 | 37.0 | 32.9 | 63.4 | 58.1 | 54.1 | 56.1 | 55.7 | 51.2 | 51.6 | 56.9 | 70.3 | 68.3 | 63.0 |

The data show that the present zeolite is effective in converting the model durene/benzene feed. Between 315-427° C. (600-800° F.), a range of durene conversions of from 33-70% was observed. Selectivities for toluene ranged from 3-13% and selectivities for xylenes ranged from 1-5%.

What is claimed is:

1. A process for reducing the durene content of a durene-containing effluent or durene-containing fraction thereof resulting from the zeolite-catalyzed conversion of at least one $C_1$-$C_4$ oxygenate to gasoline which comprises contacting said durene-containing effluent or durene-containing fraction under durene conversion conditions with a durene conversion catalyst to convert the durene to one or more products selected from the group consisting of toluene, zylenes, trimethylbenzenes, ethylbenzene and ethyltoluenes, said catalyst comprising a synthetic porous crystalline material characterized by an x-ray diffraction pattern including values substantially as set forth in Table A of the specification.

2. The process of claim 1 wherein the synthetic porous crystalline material is characterized by an X-ray diffraction pattern including values substantially as set forth in Table B of the specification.

3. The process of claim 1 wherein the synthetic porous crystalline material is characterized by an X-ray diffraction pattern including values substantially as set forth in Table C of the specification.

4. The process of claim 1 wherein the synthetic porous crystalline material is characterized by an X-ray diffraction pattern including values substantially as set forth in Table D of the specification.

5. The process of claim 1 wherein the synthetic porous crystalline material has a composition comprising the molar relationship $$X_2O_3:(n)YO_2,$$

wherein n is at least about 10, X is a trivalent element and Y is a tetravalent element.

6. The process of claim 2 wherein the synthetic porous crystalline material has a composition comprising the molar relationship:

$$X_2O_3:(n)YO_2,$$

wherein n is at least about 10, X is a trivalent element and Y is a tetravalent element.

7. The process of claim 3 wherein the synthetic porous crystalline material has a composition comprising the molar relationship $$X_2O_3:(n)YO_2,$$

wherein n is at least about 10, X is a trivalent element and Y is a tetravalent element.

8. The process of claim 4 wherein the synthetic porous crystalline material has a composition comprising the molar relationship $$X_2O_3:(n)YO_2,$$

wherein n is at least about 10, X is a trivalent element and Y is a tetravalent element.

9. The process of the claim 1 wherein the synthetic porous crystalline material possesses equilibrium adsorption capacities of greater than about 4.5 wt.% for cyclohexane vapor and greater than about 10 wt.% for n-hexane vapor.

10. The process of claim 5 wherein X is selected from the group consisting of aluminum, boron, gallium and combinations thereof and Y is selected from the group consisting of silicon, germanium and combinations thereof.

11. The process of claim 5 wherein X comprises aluminum and Y comprises silicon.

12. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

13. The process of claim 1 wherein said synthetic porous crystalline material has been thermally treated at a temperature up to about 925 ° C. in the presence or absence of steam.

14. The process of claim 12 wherein said synthetic porous crystalline material has been thermally treated at a temperature up to about 925° C. in the presence or absence of steam.

15. The process of claim 1 wherein said synthetic porous crystalline material is combined with a matrix material.

16. The process of claim 15 wherein said matrix material is selected from the group consisting of silica-containing material, alumina-containing material, zirconia-containing material, titania-containing material, magnesia-containing material, beryllia-containing material, thoria-containing material, and combinations thereof.

17. The process of claim 1 wherein the durene conversion conditions include a temperature of from about 200 to about 1000° F., a pressure of from about 0 to about 1000 psig, a hydrogen to hydrocarbon mole ratio of from about 0 to about 10 and a weight hourly space velocity of from about 0.1 to about 100.

18. The process of claim 1 wherein the durene conversion conditions include a temperature of from about 600 to about 900° F., a pressure of from about 15 to about 300 psig, a hydrogen to hydrocarbon mole ratio of from about 1 to about 3 and a weight hourly space velocity of from about 0.1 to about 10.

19. The process of claim 1 wherein said durene-containing fraction has a boiling point of from about 200 to about 400° F.

20. The process of claim 1 wherein said durene-containing fraction has a boiling point of from about 300 to about 400° F.

21. The process of claim 1 wherein said durene-containing fraction has a boiling point of from about 350° to about 400° F.

* * * * *